United States Patent
Gregg et al.

(10) Patent No.: US 10,314,723 B2
(45) Date of Patent: Jun. 11, 2019

(54) EFFECTIVE SHAPE CONTROLLER FOR LOWER LIMB

(71) Applicant: Rehabilitation Institute of Chicago, Chicago, IL (US)

(72) Inventors: Robert D. Gregg, Allen, TX (US); Jon Sensinger, Chicago, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 0 days.

(21) Appl. No.: 14/286,380

(22) Filed: May 23, 2014

(65) Prior Publication Data

US 2014/0364962 A1 Dec. 11, 2014

Related U.S. Application Data

(60) Provisional application No. 61/826,961, filed on May 23, 2013.

(51) Int. Cl.

| | | |
|---|---|---|
| *A61F 2/68* | (2006.01) | |
| *A61F 2/66* | (2006.01) | |
| *A61F 2/64* | (2006.01) | |
| A61F 2/60 | (2006.01) | |
| A61F 2/70 | (2006.01) | |
| A61F 2/76 | (2006.01) | |

(52) U.S. Cl.
CPC .............. *A61F 2/6607* (2013.01); *A61F 2/64* (2013.01); *A61F 2/68* (2013.01); *A61F 2002/607* (2013.01); *A61F 2002/704* (2013.01); *A61F 2002/7625* (2013.01); *A61F 2002/7635* (2013.01); *A61F 2002/7645* (2013.01)

(58) Field of Classification Search
CPC .. A61F 2/6607; A61F 2/68; A61F 2/64; A61F 2002/6827; A61F 2/66
See application file for complete search history.

(56) References Cited

U.S. PATENT DOCUMENTS

| | | | |
|---|---|---|---|
| 7,431,737 B2 | 10/2008 | Ragnarsdottir | |
| 7,896,927 B2 | 3/2011 | Clausen | |
| 8,403,997 B2 * | 3/2013 | Sykes | A61F 2/68 623/24 |
| 8,801,802 B2 * | 8/2014 | Oddsson | A61F 2/68 623/24 |

(Continued)

OTHER PUBLICATIONS

Eilenberg, Michael F., et al., Control of a Powered Ankle-Food Prosthesis Based on a Neuromuscular Model, IEEE Transactions on Neural Systems and Rehabilitation Engineering, Apr. 2010, pp. 164-173, vol. 18 No. 2.

(Continued)

*Primary Examiner* — Bruce E Snow
(74) *Attorney, Agent, or Firm* — Polsinelli PC; Ari M. Bai

(57) ABSTRACT

Systems and methods for improved control of a lower limb device are disclosed. The lower limb may have one or more joints and one or more corresponding motors. In some embodiments, a center of pressure is calculated in order to enforce virtual constraints at the one or more joints of the lower limb device. The system utilizes one or more effective shapes, and each effective shape's corresponding error, in order to cause each joint motor to produce a torque that causes the joint to move according to a virtual constraint. The systems and methods result in improved control of lower limb devices.

24 Claims, 11 Drawing Sheets

(56) References Cited

U.S. PATENT DOCUMENTS

Figure 1:
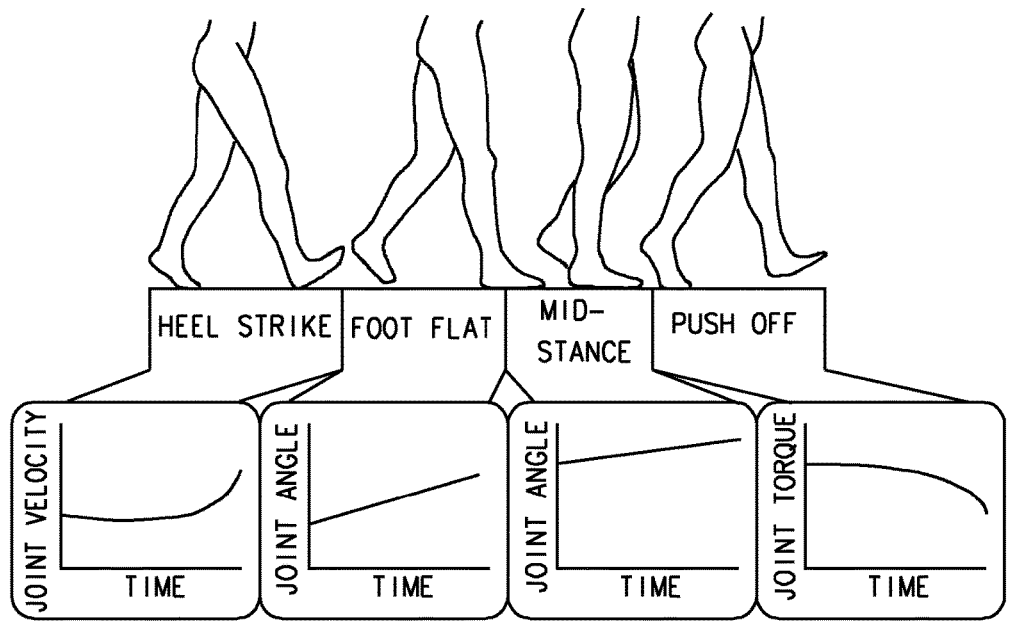

| | | | | |
|---|---|---|---|---|
| 8,974,543 | B2* | 3/2015 | Balboni | A61F 2/68 623/43 |
| 9,060,884 | B2* | 6/2015 | Langlois | A61F 2/68 |
| 2006/0122710 | A1* | 6/2006 | Bedard | A61F 2/644 623/24 |
| 2008/0097269 | A1* | 4/2008 | Weinberg | A61F 2/68 602/16 |
| 2010/0324699 | A1* | 12/2010 | Herr | A61F 2/66 623/27 |
| 2014/0081424 | A1* | 3/2014 | Herr | A61F 2/60 623/50 |
| 2015/0018972 | A1* | 1/2015 | Albrecht-Laatsch | A61F 2/64 623/25 |
| 2015/0051710 | A1* | 2/2015 | Herr | A61F 2/66 623/27 |

OTHER PUBLICATIONS

Sup, Frank, et al., Preliminary Evaluations of a Self-Contained Anthropomorphic Transfemoral Prosthesis, IEEE/ASME Transactions on Mechatronics, Dec. 2009, pp. 667-676, vol. 14 No. 6.

Sup, Frank, et al., Upslope Walking With a Powered Knee and Ankle Prosthesis: Initial Results With an Amputee Subject, IEEE Transactions on Neural Systems and Rehabilitation Engineering, Feb. 2011, pp. 71-78, vol. 19 No. 1.

Sup, Frank, et al., Design and Control of a Powered Transfemoral Prosthesis, The International Journal of Robotics Research, Feb. 2008, pp. 263-273, vol. 27, No. 2, SAGE Publications, Los Angeles, London, New Delhi, and Singapore.

Steeper USA, Multi-Flex Wrist for bebionic3, 2013, Issue 1, San Antonio.

Holgate, Matthew A., et al., A Novel Control Algorithm for Wearable Robotics using Phase Plane Invariants, 2009 IEEE International Conference on Robotics and Automation, May 2009, pp. 3845-3850, Kobe, Japan.

RSL Steeper, Upper Limb Prosthetic Components, 2014, Issue 1, United Kingdom.

RSL Steeper, bebionic3 technical information, 2014, Issue 4, United Kingdom.

Hansen, Andrew H. et al., Investigations of roll-over shape: implications for design, alignment, and evaluation of ankle-foot prostheses and orthoses, Disability and Rehabilitation, 2010, pp. 2201-2209, vol. 32:26.

* cited by examiner

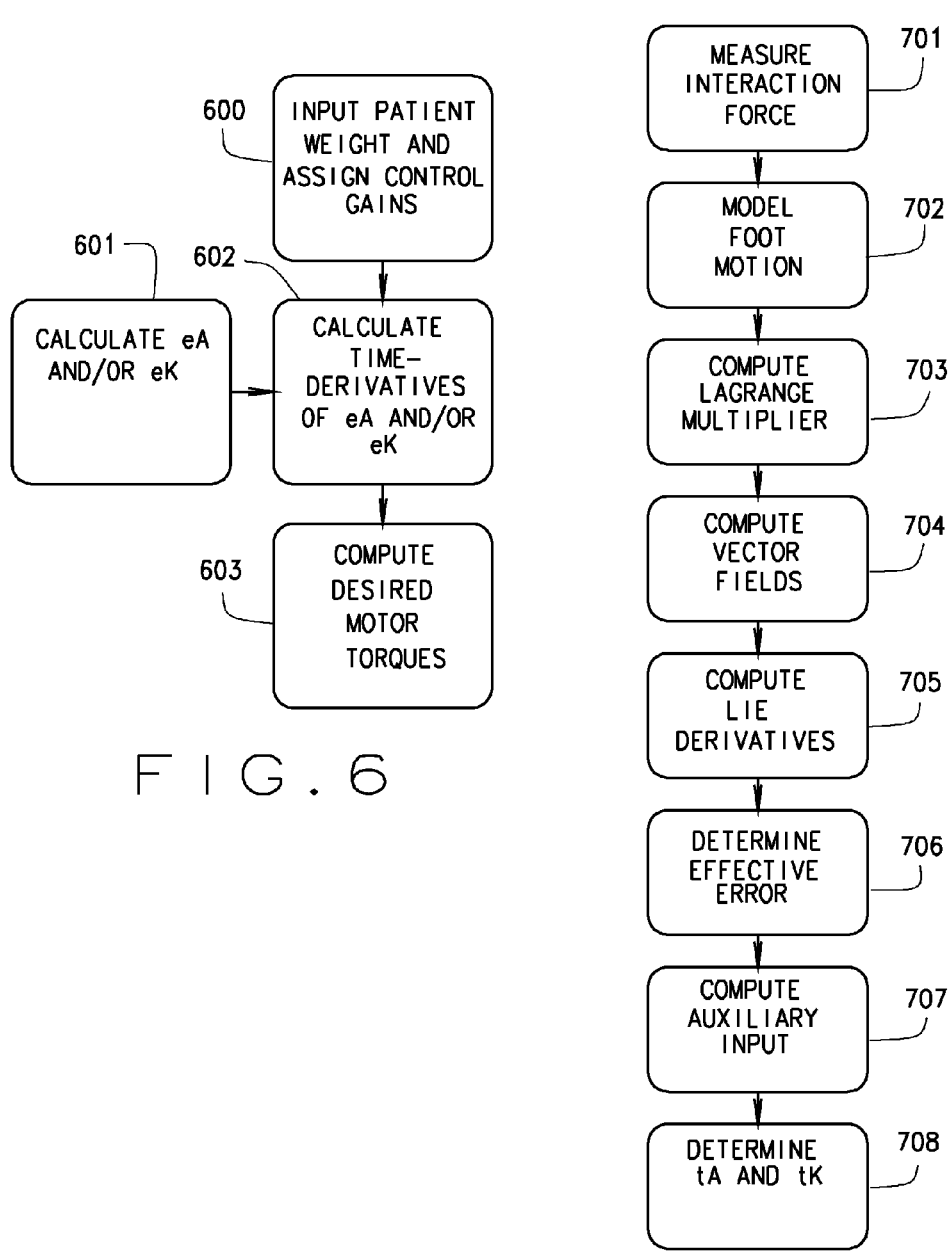

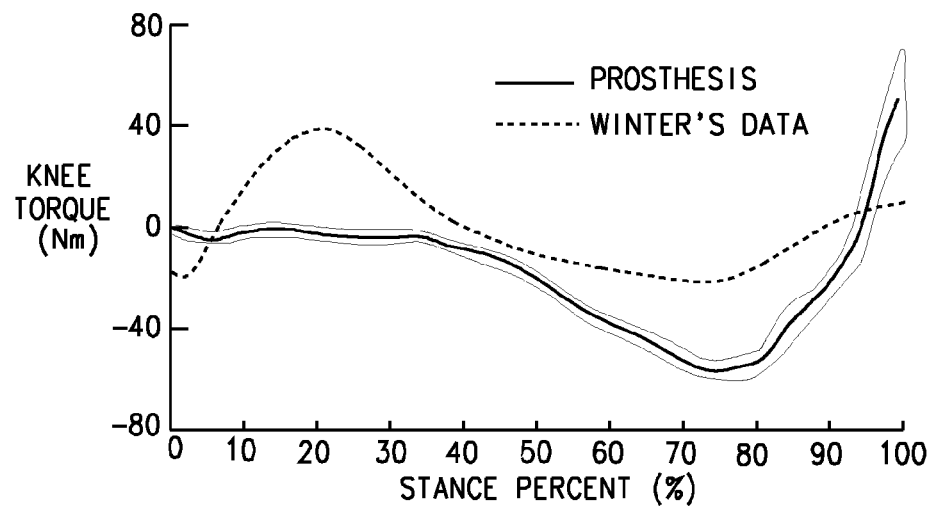
F I G . 8A
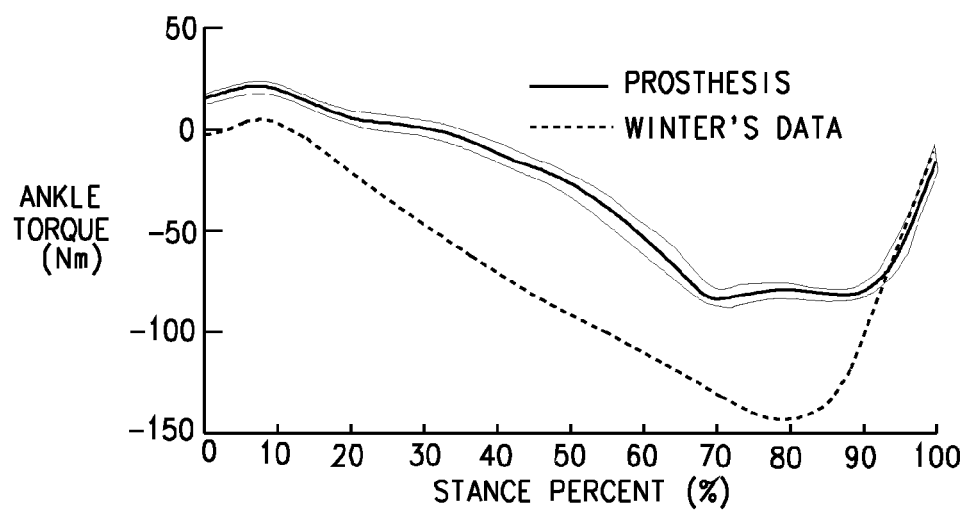
F I G . 8B

EFFECTIVE SHAPE CONTROLLER FOR LOWER LIMB

GOVERNMENT LICENSE RIGHTS

This invention was made with government support under W81XWH-09-2-0020 awarded by the United States Army. The government has certain rights in the invention.

BACKGROUND OF THE INVENTION

In the field of prosthetics and orthotics (P&O), lower limb devices, such as prostheses, exist that allow increased mobility for amputees or other individuals without a lower limb (herein referred to generally as "amputees"). Lower limb devices, such as orthoses and exoskeletons, allow increased mobility for individuals who have suffered a stroke, a spinal cord injury, or other condition impairing the lower limbs, or who suffer a disease, such as peripheral neuropathy, that limits the full use of one or more lower limbs.

Some lower limb devices are passive, requiring amputees to expend far more energy performing tasks, such as standing, walking, running, or climbing stairs, than a fully-limbed individual would otherwise expend. Other lower limb devices are powered, offering amputees the promise of regaining the ability to perform all tasks that a sound-limbed individual can perform, including standing, walking, running, and climbing stairs. A powered lower limb device uses motors to apply torques to one or more joints in the limb, causing the joint to flex or stiffen with applied levels of power and therefore assisting a user's movement during a task. The pattern of motion repeating from step to step during a task or other locomotion is called a "gait." A gait may be divided into a "stance" phase, wherein the foot of the leg is in contact with the ground, and a "swing" phase, wherein the foot of the leg is not in contact with the ground. The stance phase and the swing phase each may be divided into more discrete phases; for instance, swing phase may be divided into early swing phase (knee flexion) and late swing phase (knee extension).

Powered lower limb devices include a microprocessor that is programmed with a control system for the control of the device. Control systems known in the art for powered lower limb prostheses rely on various strategies. One control system relies on information from sensors coupled to the lower limb device, which provide real-time information about the present joint angles, velocities, and torques when the device is in operation. The control system compares information received from sensors to a look-up table of desired joint angles, velocities, or torques over time. One disadvantage of this system is that it is not adaptable to varying tasks or conditions. The look-up table is based on a gait cycle that has been divided into multiple time periods, each termed "phases," that have observable behaviors. An example of a "phase" is when the ankle pushes off at the end of a step cycle, as shown in FIG. 1. In the prior art, a prosthetic leg sequentially mimics human behavior by implementing a different control model for each discrete phase of gait. FIG. 1 further shows how the velocity, angle, and torque depend on a time variable set in each phase of the gait cycle, in the prior art. This prior art approach requires each controller to be manually tuned and is not robust to external perturbations that push joint kinematics (i.e., angles and velocities) forward or backward in the gait cycle, which cause the wrong controller to be used.

Prior art systems that rely on segmentation of the gait cycle employ a variety of control strategies, which may enforce different reference trajectories, joint impedances (the "impedance" of a joint being a measurement of its stiffness/viscosity), and/or reflex models, based on discrete phases of the gait cycle. Such control systems are disclosed in the following articles, which are incorporated by reference: F. Sup, A. Bohara, and M. Goldfarb, "Design and control of a powered transfemoral prosthesis," *Int J Rob Res*, vol. 27, pp. 263-273, Feb. 1, 2008; F. Sup, H. A. Varol, and M. Goldfarb, "Upslope walking with a powered knee and ankle prosthesis: initial results with an amputee subject," *IEEE transactions on neural systems and rehabilitation engineering*, vol. 19, pp. 71-8, February 2011; M. F. Eilenberg, H. Geyer, and H. Herr, "Control of a powered ankle-foot prosthesis based on a neuromuscular model," *IEEE Transactions on Neural Systems and Rehabilitation Engineering*, vol. 18, pp. 164-73, April 2010; and K. A. Shorter, G. F. Kogler, E. Loth, W. K. Durfee, and E. T. Hsiao-Wecksler, "A portable powered ankle-foot orthosis for rehabilitation," *J Rehabil Res Dev*, vol. 48, pp. 459-72, 2011. One disadvantage of these control systems is that a highly-trained clinician must spend significant amounts of time to finely tune multiple control parameters for each individual user. These powered lower limb prostheses have many parameters that must be tuned for stance, including parameters relating to sequential impedance control, a joint muscle model, or lookup tables for tracking human data. Having multiple parameters that require precise tuning contributes substantially to the expense of a powered lower limb device.

Another disadvantage of current powered lower limb devices is that the control strategies do not fully account for the natural walking shape that a natural lower limb employs during tasks. As a result, powered lower limb devices employing such control strategies can cause discomfort and instability to their users. The natural walking shape can be approximated by the "effective shape." The effective shape is the trajectory of the center of pressure (or "COP", described below) mapped into a moving reference frame attached to the stance leg. The effective shape is called the rollover shape during walking. For a rigid object, such as a metal wheel, the effective shape is its actual geometry. Objects that are not rigid, such as an ankle or other joint, have a variable effective shape that can be controlled within a local coordinate frame, such as that of the shank or thigh. The effective shape of a human's able-bodied lower limb remains invariant across many conditions, including heel height, walking speed, and body weight. In other words, the effective shape does not change in response to changes in these conditions. The effective shape of an able-bodied lower limb changes between different tasks. For example, the curvature of the effective shape of a lower limb when performing a walking task differs from the curvature of the effective shape of a lower limb when performing a stationary standing task. Likewise, upstairs climbing requires yet another different effective shape. Each effective shape can be characterized by the curvature of the COP trajectory with respect to a reference frame attached to the stance leg. The COP is the point on the plantar sole of a foot where the cumulative reaction force is imparted against the ground. See A. H. Hansen and D. S. Childress, "Investigations of roll-over shape: implications for design, alignment, and evaluation of ankle-foot prostheses and orthoses," *Disabil Rehabil*, vol. 32, pp. 2201-9, 2010, which is incorporated by reference.

Certain prior art systems make limited use of the COP. The "Shape & Roll" is a passive foot prosthesis, the bottom of which is made with rubber or other flexible material, with periodic gaps in material across the bottom of the sole. When an amputee walks on the Shape & Roll, the pressure at the COP compresses the rubber or other flexible material into the gaps, enforcing an effective shape that mirrors the natural walking shape of a sound leg. In addition to being a passive system, the Shape & Roll foot cannot enforce more than one effective shape, limiting its usability for individuals who want to perform more than one task (such as walking and climbing stairs). The Shape & Roll foot does not provide knee control, for above-knee amputees. The Genium prosthetic leg is a passive, microcontrolled leg that uses the COP during the user configuration process but does not use COP for active control. Certain humanoid robots employ strategies that attempt to control the COP so that it stays near the center of the foot, away from the edges, in order to prevent foot rotation and thus prevent falls, but does not measure the COP as a phase variable for controlling the progression of joint patterns. Bipedal robots are known that can walk, run, and climb stairs using a control framework that uses sensor measurements and actuators to produce joint torques. See E. R. Westervelt, J. W. Grizzle, C. Chevallereau, J. H. Choi, and B. Morris, Feedback Control of Dynamic Bipedal Robot Locomotion (New York, N.Y.: CRC Press, 2007), incorporated by reference. The control system employed by these bipedal robots uses a monotonic physical variable to control movement. The monotonic variable serves as a unique representation of the phase (or timing) in the gait cycle (the period between ground-strike events of the same leg). Therefore, the phase variable parameterizes a nonlinear control model to create appropriate phase-specific behaviors. Calculation of the monotonic variable relies on data from joint encoders for multiple joints of the robot. Such a strategy is not feasible in the design of a lower limb device like a prosthesis, orthosis, or exoskeleton, where clinical application of the device precludes attachment of multiple sensors to the sound joints of the user, significantly limiting measurement and control as a result.

One prior art prosthetic ankle employs a combination of the shank angle and velocity to track able-bodied human data on the basis of a look-up table of pre-defined reference trajectories. As a result, the ankle is not adaptable to varying conditions or tasks. The ankle also relies on measurements from gyroscopes, which are difficult to implement due to sensor drift and delay from filtering. The ankle cannot be used effectively by above-knee amputees, who do not have a knee joint.

Other prior art prostheses use mechanical or hydraulic means to cause the knee joint to move in response to a force initiated at the ankle One system, known as the Hydracadence knee (Proteor: Dijon, France), relies on the physical force of fluid pushed between ankle and knee for joint control.

SUMMARY OF THE INVENTION

The present invention relates to a controller that implements a control system for a lower limb device based on a determination of a virtual constraint. The present invention also relates to a lower limb device that implements such a controller. A virtual constraint, as used herein, is a rule applied by the control system in a controller that causes a lower limb device to adjust its joint elements, such as position, velocity, or torque, in response to the value of a monotonic (e.g., strictly increasing) mechanical variable, or "phase variable."

In embodiments of the present invention, the virtual constraint utilized by the control system is the effective shape.

In embodiments of the present invention, the effective shape is determined using the COP, which moves monotonically from heel to toe during the stance phase of certain tasks.

In embodiments of the present invention, the effective shape is determined using a monotonic variable other than the COP during other gaits, such as stair climbing, where the COP is not monotonic.

In embodiments of the present invention, the effective shape is used to calculate the torque applied by motors coupled to the joints of a lower limb device.

In embodiments of the present invention, the effective shape is used to calculate the torque using a first torque controller described herein.

In embodiments of the present invention, the effective shape is used to calculate the torque using a second torque controller described herein.

In embodiments of the present invention, control of multiple joints in a lower limb device is done in a coordinated fashion through a unifying control strategy, rather than through multiple task-specific approaches that depend on pre-defined reference trajectories or approaches that control each joint's movement separately.

In embodiments of the present invention, the control strategy employed results in the ankle providing additional torque and power in the push off phase of gait.

An advantage of some of the embodiments described herein is that the lower limb device can be used without requiring individual configuration of a user's heel height, walking speed, body weight, or other variable conditions.

An advantage of the embodiments described herein is that they require relatively little time, effort, or knowledge to tune the control parameters of a powered limb, therefore improving clinical viability.

An advantage of the embodiments described herein is that both the knee and the ankle of the prosthesis are controlled by a single control strategy, resulting in human-like patterns of movement and robustness to small perturbations.

BRIEF DESCRIPTIONS OF THE DRAWINGS

FIG. 1 displays gait phases used in the prior art to control lower limb devices.

Figure 2:
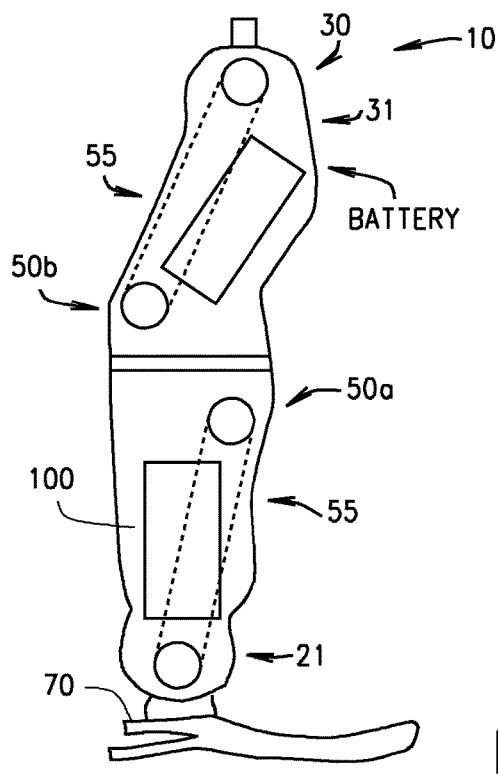

FIG. 2 displays a prosthetic leg programmed with the control strategies described herein.

Figure 3:
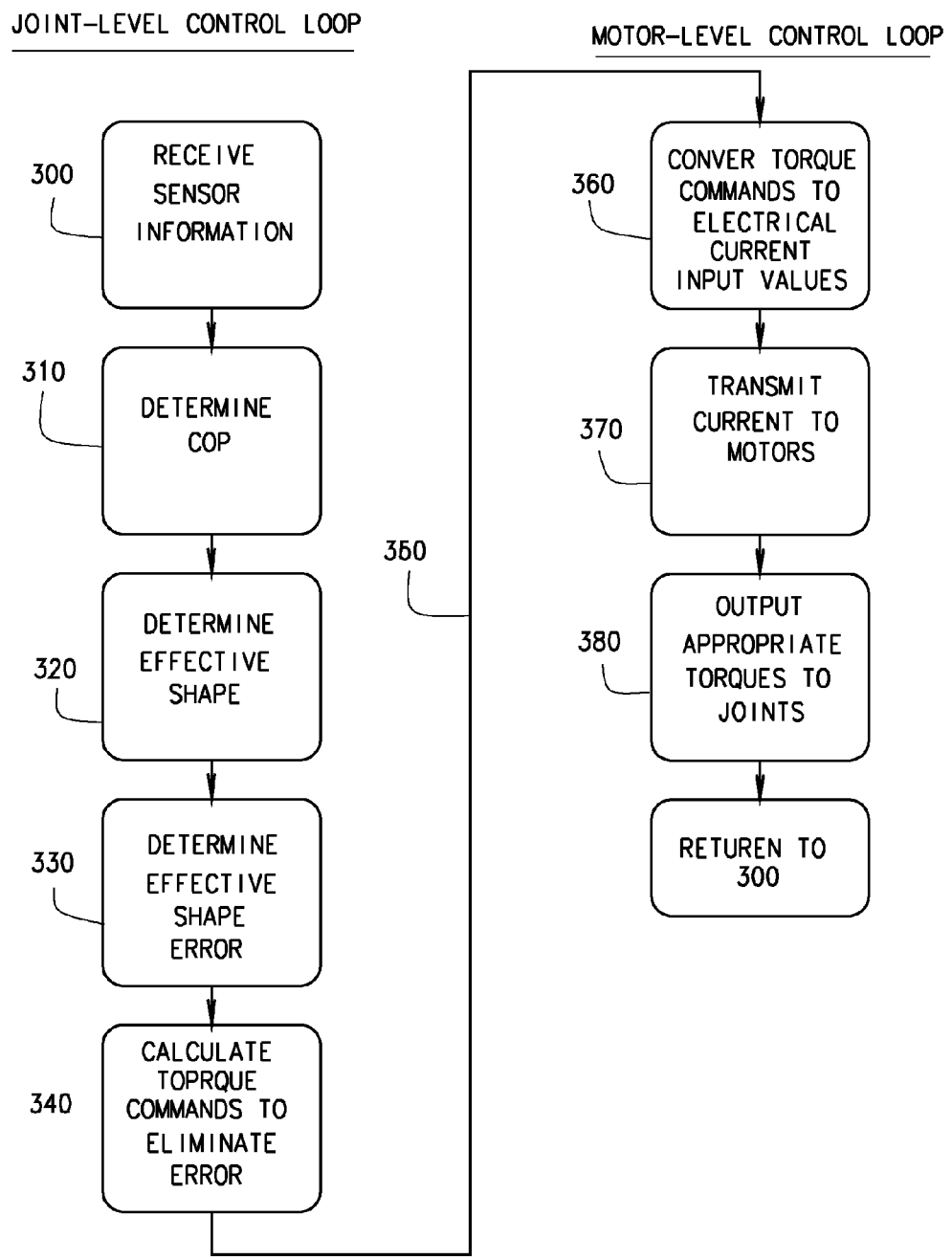

FIG. 3 displays a flow chart of the control strategies described herein.

Figure 4A:
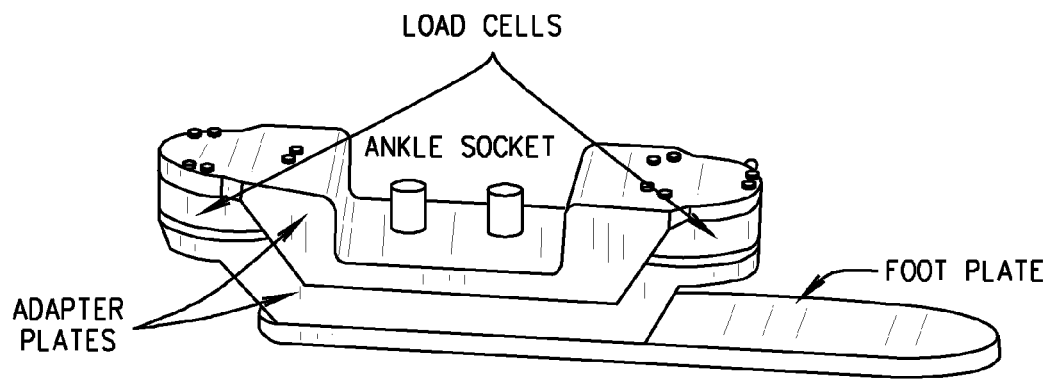
Figure 4B:
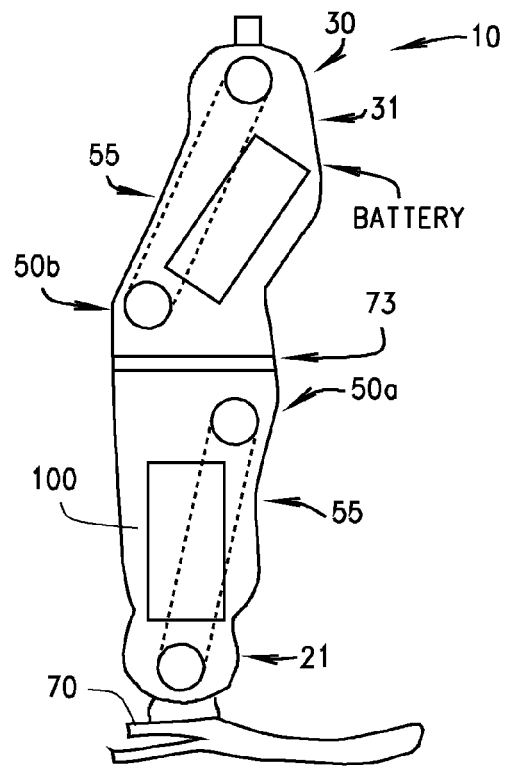

FIG. 4A displays an instrumented foot, comprising a load cell adapter mounted on a carbon fiber prosthetic foot plate. FIG. 4B displays an instrumented limb with a load cell system.

Figure 5:
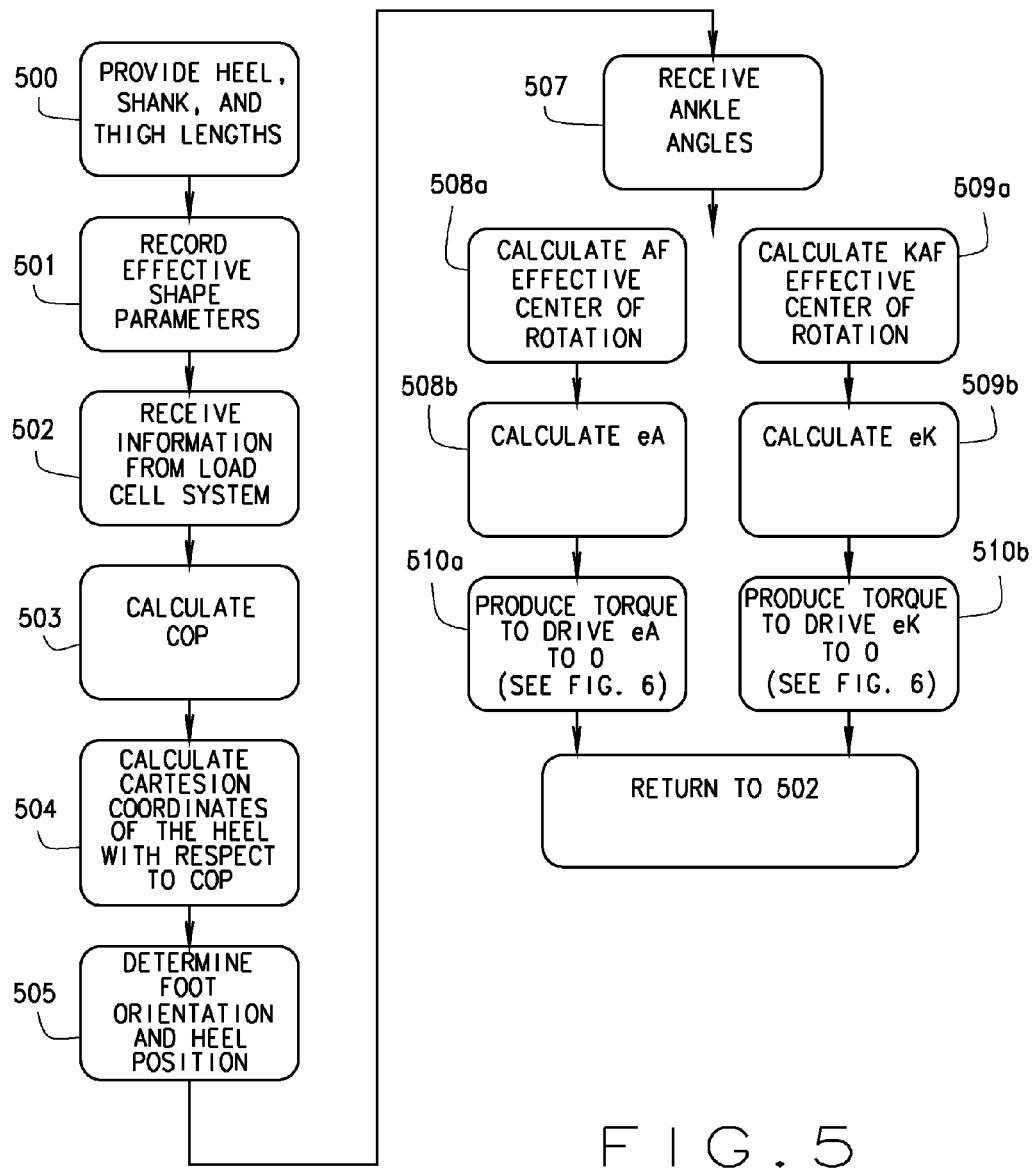

FIG. 5 displays a flow chart of the control strategies described herein relating to effective shape.

FIG. 6 displays a flow chart of the control strategies described herein relating to producing joint torques utilizing a PD controller.

FIG. 7 displays a flow chart of the control strategies described herein relating to producing joint torques utilizing a feedback linearization controller.

FIGS. 8A and 8B display graphs of torque profiles produced by a limb utilizing control strategies described herein.

Figure 9:
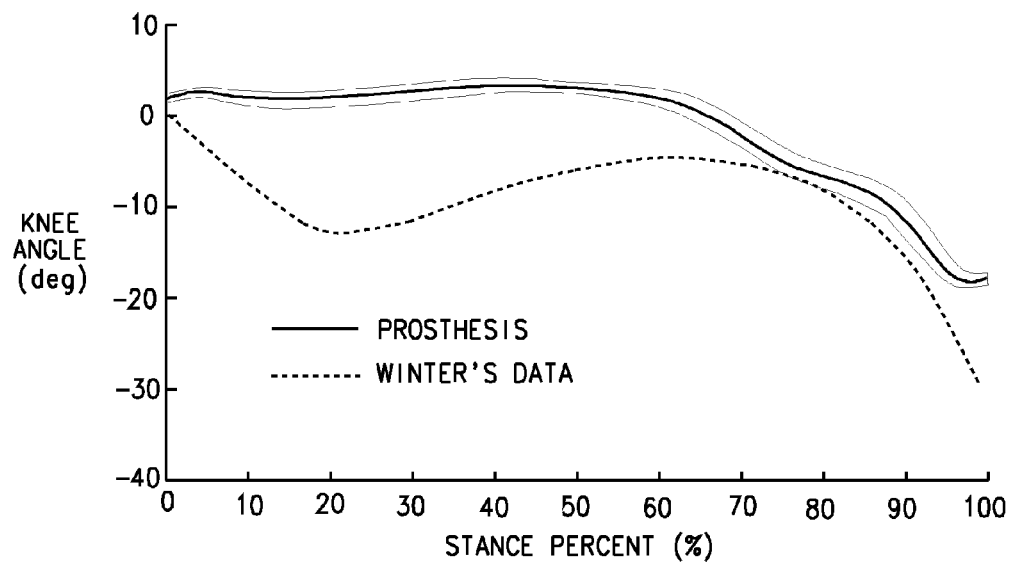

FIG. 9 displays a graph of knee flexion produced by a limb utilizing control strategies described herein.

Figure 10:
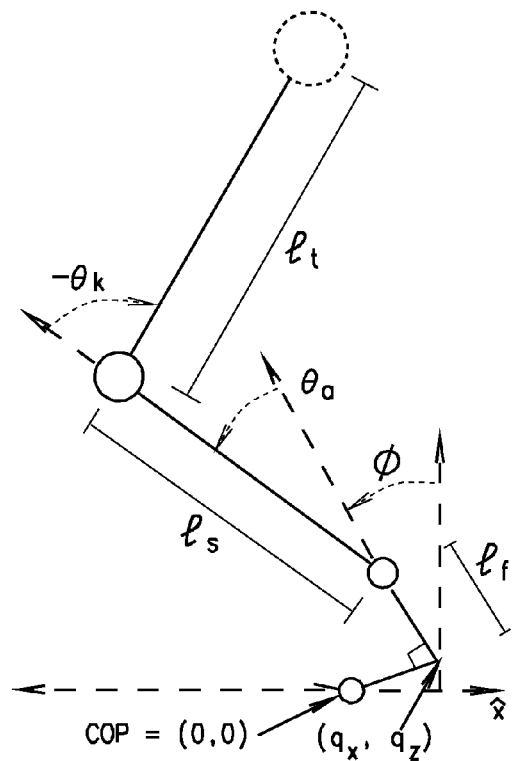

FIG. 10 displays the kinematic model of a transfemoral prosthetic leg with human subject's hip joint shown as a dashed circle. Positive/negative movements are respectively termed dorsiflexion/plantarflexion for the ankle and extension/flexion for the knee.

Figure 11:
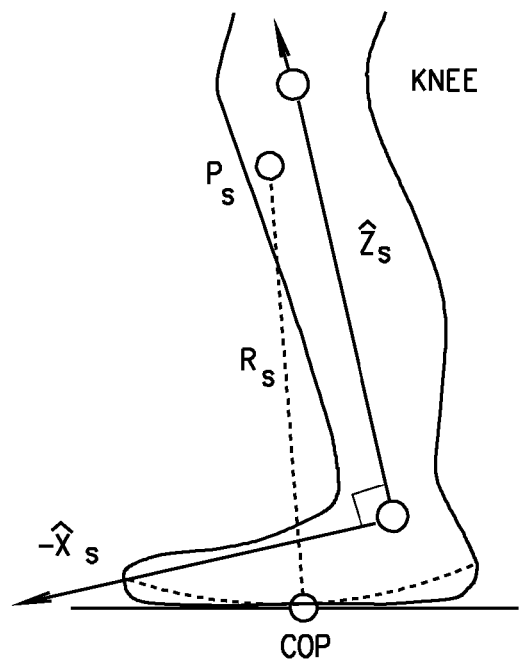

FIG. 11 displays a diagram of the ankle-foot effective shape. The COP is indicated by the dashed curve in the shank-based or thigh-based coordinate frame (solid axes).

Figure 12:
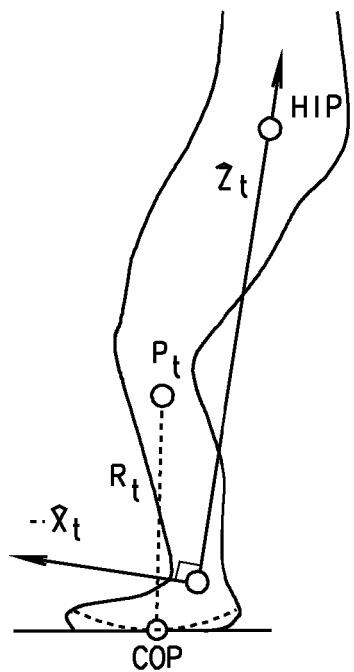

FIG. 12 displays a diagram of the knee-ankle-foot effective shape. The COP is indicated by the dashed curve in the shank-based or thigh-based coordinate frame (solid axes).

Figure 13:
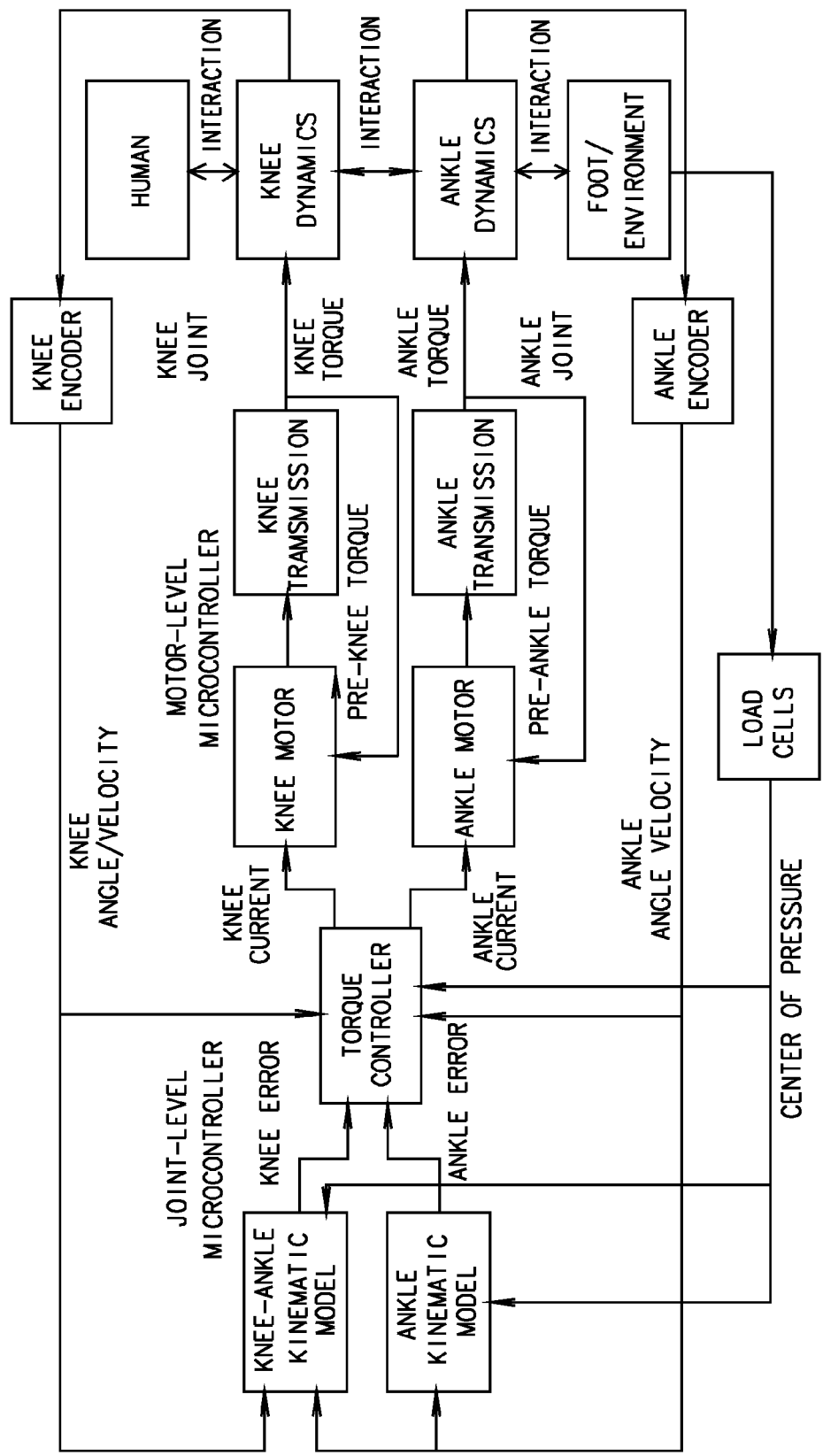
Figure 14A:
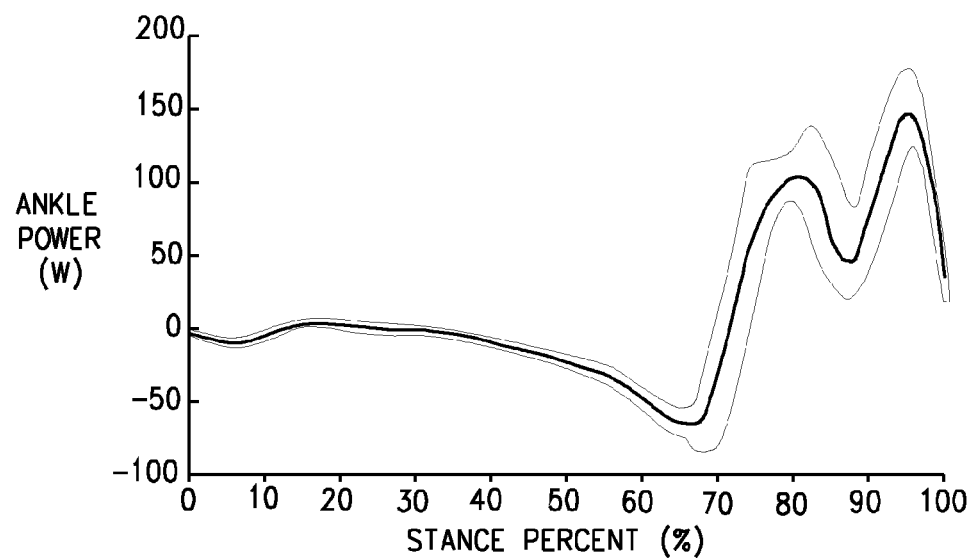
Figure 14B:
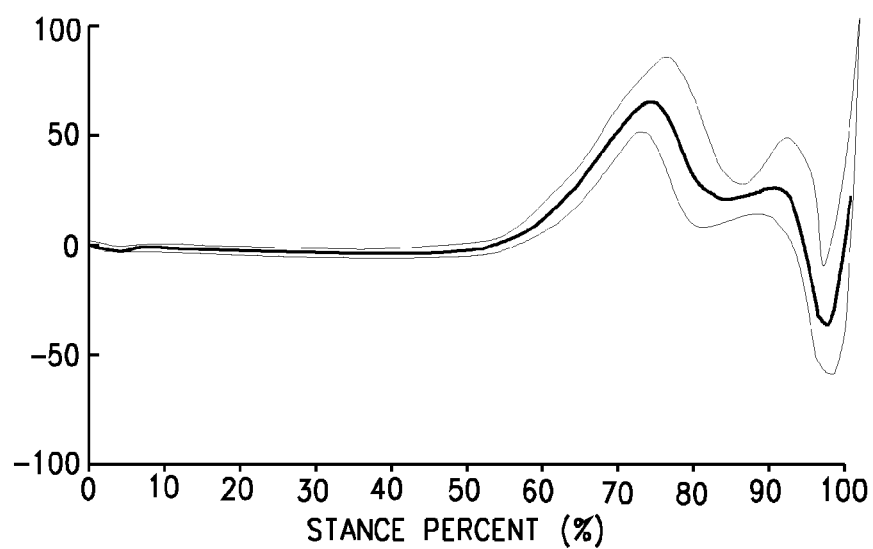

FIG. 13 displays a flow chart indicating interaction among different components of the embodiments described herein FIGS. 14A and 14B display mechanical power plots for the knee and ankle using embodiments of the control systems described herein.

Figure 15A:
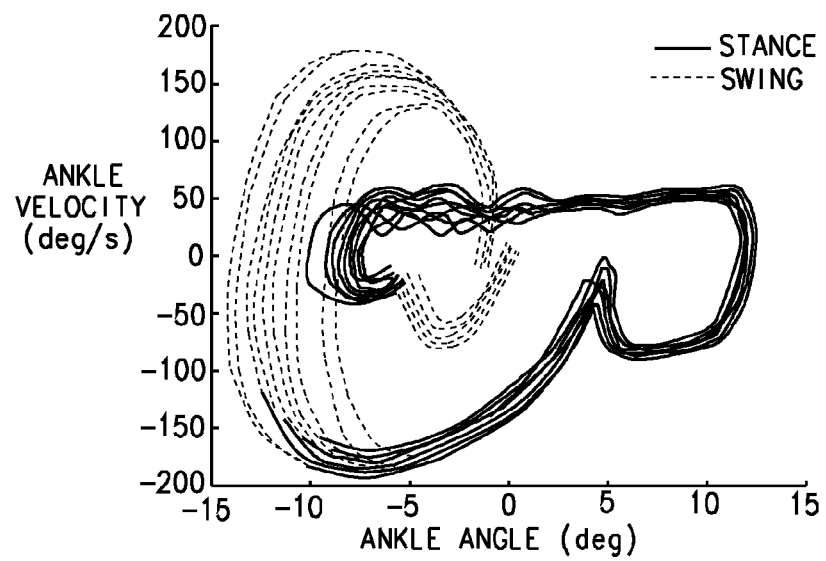
Figure 15B:
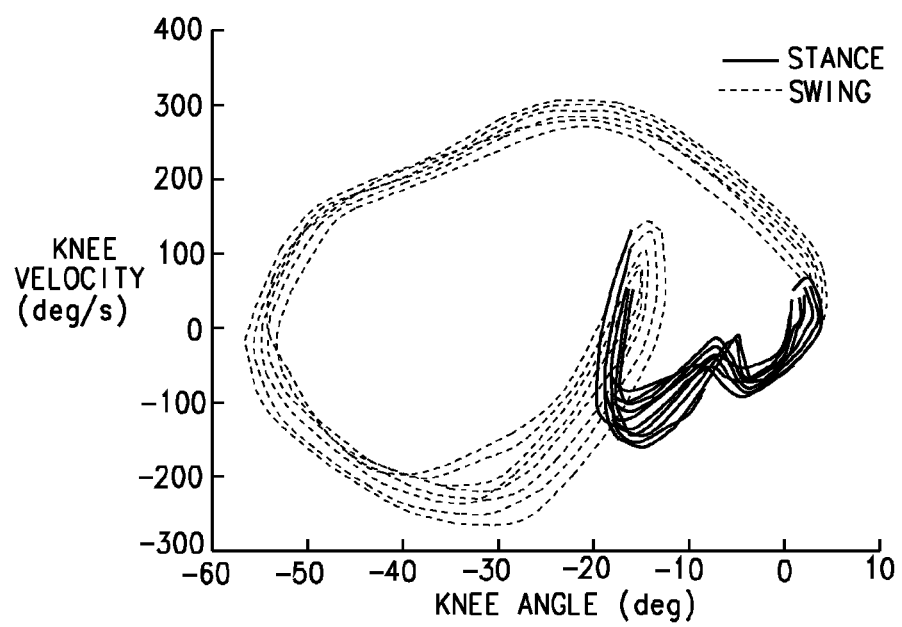

FIG. 15A displays a plot of ankle angle against ankle velocity and FIG. 15B displays a plot of knee angle against knee velocity.

LIST OF DRAWING DETAILS 5 contralateral leg
10 Prosthetic limb
15 Leg
20 Ankle
21 Ankle joint
30 Knee
31 Knee joint
35 Strain gages
40 Encoders
45 Ammeters
50 Motors
50a Ankle motor
50b Knee motor
55 Transmissions
60 Socket load sensor
70 Foot
71 Sole
72 Top plate
73 Load cell system
73A Toe load cell
73B Heel load cell
74 Inertial measurement unit
75 Bottom plate
100 Microcontroller
110 Motor-level current loop
120 Joint-level loop
130 Signal conditioning box

DETAILED DESCRIPTION OF THE EMBODIMENTS

Embodiments of the present invention will now be discussed with reference to the figures.

FIG. 2 discloses a prosthetic limb 10 that may be programmed according to the control methods described herein. Limb 10 comprises a powered ankle 20 and powered knee 30. Each joint is coupled to an encoder 40 that can measure the joint's angle and velocity. Each joint is also coupled to a motor 50 and transmission 55 that together are capable of producing physiological levels of torque. 50a indicates the motor coupled to the ankle and 50b indicates the motor coupled to the knee. For a user weighing up to 90 kg, at least 80 Nm of torque is preferred. Limb 10 and its related components may be the prosthetic limb with powered knee and ankle joints developed by the Vanderbilt Center for Intelligent Mechatronics (Vanderbilt University, TN) and commercialized by Freedom Innovations (Irvine, Calif.) or another powered prosthetic limb. Limb 10 and its components are powered by a battery.

Limb 10 includes microcontroller 100 that is programmed to run two control loops, a motor-level control loop 110 and a joint-level control loop 120. Microcontroller 100 should have an update rate of at least 500 Hz and preferably 1 kHz or more. If microcontroller 100 accepts only impedance commands (i.e. stiffness Kp, viscosity Kd, and equilibrium angle Theta), its impedance controller can be replaced by a desired virtual constraint controller. This is done for each joint by sending the microcontroller 100 any standard Kp and Kd values and an equilibrium angle given by Theta=Joint_Angle+(Kd*Joint_Velocity+Torque_Desired)/Kp, where Torque_Desired is the torque calculated from sensor measurements by a torque controller, such as one of the torque controllers described herein. The joint-level loop 120 calculates and re-sends the equilibrium angle for each joint at the same frequency at which the motor-level loop 110 operates.

Microcontroller 100 is programmed with a control strategy for the control of prosthesis 10. FIG. 3 discloses a flow chart for the operation of limb 10 when it is in use in stance phase. In 300, joint-level control loop 120 receives sensor information, including from a load cell system. In 310, joint-level control loop 120 calculates the COP. In 320, joint level control loop 120 uses the COP to calculate the effective shape of the prosthetic limb. In 330, joint-level control loop 120 determines the effective shape error. In 340, joint-level control loop 120 uses the effective shape error to calculate appropriate torque commands, in an effort to eliminate the effective shape error so that the effective shape of prosthesis 10 closely mirrors the natural shape of a sound limb. In 350, joint-level control loop 120 transmits the torque commands to motor-level control loop 110. In 360, motor-level control loop 110 converts the torque commands to electrical current input values that reflect the amount of current to be applied to the motors 50. In 370, motor-level control loop 110 causes current to flow to motors 50 on the basis of the current input values. In optional 370a (not shown), reflecting closed-loop control, ammeters 45 measure the current flowing to motors 50 and current flow may be corrected to the desired level if needed. In 380, motors 50 and transmissions 55 output the appropriate torques to ankle joint 21 and knee joint 31. In optional 380a (not shown), again reflecting closed-loop control, strain gages 35 may measure torques at ankle 21 and knee 31 and current flow may be corrected to achieve intended torque control. After step 380 (or optional step 380a), the microcontroller 100 returns to step 300.

In one embodiment, microcontroller 100 comprises two microcontrollers, microcontroller 100M that implements motor-level control loop 110 and microcontroller 100J that that implements joint-level control loop 120. The PIC32 (Microchip Technologies Inc., Chandler, Ariz.) or a similar microcontroller may be used for each of 100M and 100J. Microcontrollers 100M and 100J communicate over the CAN protocol or another digital medium. Microcontroller 100M accepts torque commands to drive motors 50. Alternately, microcontroller 100M may accept impedances instead of torque commands, in which case an additional impedance inversion stage is needed in the joint-level control loop 120. Alternately, a single microcontroller comprises microcontroller 100.

The systems and methods described herein can be used to control other powered lower limb devices besides limb 10, including orthoses or exoskeletons. The systems and methods described herein can be used to control a single joint powered lower limb device, such as an ankle prosthesis, or a multi joint powered lower limb device, such as limb 10, which includes a motorized ankle and a motorized knee. Calculation of the COP is described in detail herein, and the control systems described herein may use COP as phase variable for those tasks where COP is monotonic during the stance phase, including standing, walking on a level surface, walking uphill, walking downhill, and heel-to-toe running. For other tasks where COP is not monotonic, such as stair climbing, another monotonic variable such as the thigh position may be used as a phase variable for a repetitive task.

Determining the Center of Pressure

FIG. 4A displays an ankle joint 20 coupled to prosthetic foot 70 having load cell system 73, signals from which are used by the control system to regularly determine the COP while the limb 10 is in use. Load cells 73 comprise either one or two 3-axis load cells, which measure horizontal force, vertical force, and out-of-plane moment. In the embodiment displayed in FIG. 4A, the prosthetic foot 70 comprises two plates, top plate 72 and bottom plate 75. Top plate 72 and bottom plate 75 may be made of aluminum or another sufficiently strong light-weight material. Top plate 72 and bottom plate 75 are mounted above and below, respectively, a load cell system 73. The load cell system 73 detects the forces applied to the foot when used in walking or other tasks. In one embodiment, the load cell system 73 comprises toe load cell 73A and heel load cell 73B. Toe load cell 73A and heel load cell 73B are each capable of measuring horizontal and vertical forces in the sagittal plane and the out-of-plane moment. Load cells like the Mini45 (ATI Industrial Automation, Apex, N.C.) may be used for 73A and 73B. Using two load cells, one at the toe of prosthetic foot 70 and one at the heel of prosthetic foot 70, distributes loads encountered during walking, thus preventing sensor saturation and bending moments. In another embodiment of the prosthetic foot 70, a sufficiently strong single load cell could be used in load cell system 73.

In one embodiment, load cell system 73 is mounted below the ankle joint, e.g., using the foot adapter described herein. The top plate 72 is mounted to the bottom of the prosthetic ankle joint 21, and the bottom plate 75 is mounted to a foot plate 76 made of carbon fiber or other standard materials in the prosthetics practice. Using lightweight materials such as aluminum and carbon fiber minimizes the overall weight of the prosthetic device.

Microcontroller 100 is coupled to load cell system 73 as follows. The load cells connect to a signal conditioning box 130 via analog wires. Signal conditioning box 130, which turns the analog signals into digital data, may be of the kind offered by ATI Industrial Automation (Apex, N.C.). Signal conditioning box 130 box is connected to the microcontroller 100 via a CAN bus. Force applied to the top plate 72 and bottom plate 75 is registered by the load cell system 73, which sends load information to the signal conditioning box 130 and subsequently to microcontroller 100.

Determining the Effective Shape and Effective Shape Error

FIG. 5 is a flowchart that describes in greater detail the steps taken in order to determine the effective shape error eA and eK for the ankle and knee, respectively. It should be understood that references to microprocessor 100 in descriptions of FIG. 5 relate to operations performed in joint-level loop 120. Steps 500 and 501 reflect certain operations that occur during the initialization of one embodiment of the system. In 500, the lengths of the heel (Lf), shank (Ls), and thigh (Lt) segments of the leg are measured and provided to microcontroller 100. Such measurements may be input into microcontroller 100 by a computing device, such as a personal computer or smartphone, that is integrated into the prosthetic or coupled to it by wired or wireless means. In 501, microcontroller 100 records effective shape parameters. In one embodiment, Rs=Rt=0.158×(user height in meters) and Xs=Xt=−0.02×(user height in meters), where the static values in the prior equation come from the inventors' study of able-bodied subjects. It should be understood that other static values could be used. The rotational centers $X_s$, $X_t$ determine the amount of flexion in the ankle and knee joints, respectively, so these characteristics can be adjusted to walk on different slopes or to the user's preference.

Steps 502 and beyond reflect the steps the microprocessor repeatedly takes when limb 10 is being worn and utilized. In 502, the microprocessor 100 receives load information from load cell system 73. In 503, microcontroller 100 uses the load information from 502 to calculate COP. In one embodiment, microcontroller 100 calculates COP using the following equation, where $F_{z1}$, $F_{z2}$ are the vertical loads registered by toe load cell 73A and heel load cell 73B, respectively, and c, d are the horizontal lengths between the ankle joint 21 and each of centers of 73A and 73B, respectively:

$$COP_x = \frac{-(c^2+cd)F_{z1} + (d^2+cd)F_{z2} + dM_{y1} + dM_{y2}}{(c+d)(F_{z1}+F_{z2}) + M_{y1} - M_{y2}},$$

It should be understood that other force sensor configurations could be used to calculate the COP. In another embodiment, a grid of force-sensitive resistors is coupled to sole 71 of prosthetic foot 70. This embodiment determines COP by locating the point of greatest pressure measured among all the sensors in the grid. FIG. 4B discloses another embodiment, wherein the shank of the limb 10 comprises a 3-axis load cell 73. A kinematic model of the leg can be used to determine the COP based on forces measured at the shank and torques at the ankle. In each embodiment, the COP is defined as the point on the foot at which the net moment is zero. The net moment is the sum of all moments acting at the point, including the ankle torque, the moment arm from the vertical load at the ankle, and the moment arm from the horizontal load at the ankle. It should be apparent to one of ordinary skill in the art that microcontroller 100 could be programmed in other ways to calculate COP, based on this definition of COP.

Microcontroller 100 models the prosthetic leg as a kinematic chain with respect to a global reference frame defined at the COP during stance (as shown in FIG. 10). In 504, microcontroller 100 calculates $q_x$, $q_z$, the Cartesian coordinates of the heel defined with respect to the COP. In 505, the foot orientation and heel position are determined. In one embodiment, microprocessor 100 receives signals from inertial measurement unit 74 reflecting foot orientation and heel position. In another embodiment, microprocessor 100 approximates foot orientation and heel position using the following model:

$$q_z = L/4 - \sqrt{(L/4)^2 - q_x^2}$$

$$\phi = 2\text{sign}(q_z)\arcsin(2\sqrt{q_x^2 + q_z^2}/L)$$

for L=ls+lt, where ls is the shank length and lt is the thigh length.

The prosthetic limb 10 disclosed in FIG. 2 is controlled in response to the ankle-foot (AF) effective shape and knee-ankle-foot (KAF) effective shape. The AF effective shape is the COP trajectory mapped into a shank-based reference frame (axes $\hat{x}_S$, $\hat{z}_S$ in FIG. 11). This shape can be modeled by the distance between the COP and a point $P_S=(X_S, Z_S)^T$ in the shank-based reference frame: $\|P_S-COP\|=R_S$, where the radius of curvature $R_S$ is either constant (for tasks such as standing or walking) or is a function of the COP (for tasks such as stair climbing). The KAF effective shape is the COP trajectory transformed into a thigh-based reference frame (axes $\hat{x}_t$, $\hat{x}_t$ in FIG. 12). The KAF effective shape is characterized by the distance relationship $\|P_t-COP\|=R_t$, with center of rotation $P_t$ and radius of curvature $R_t$, which can also be a function of the COP. The AF effective shape and the KAF effective shape provide two virtual constraints to control the ankle joint and knee joint of prosthesis 10.

In 507, microcontroller 100 receives from encoders 40 the ankle angle $\Theta_a$ and knee angle $\Theta_k$ and assigns them into a vector array $q=(qx, qz, \varphi, \Theta_a, \Theta_k)^T$.

In 508a, microcontroller 100 calculates the AF effective center of rotation in the COP-based global reference frame by the function $$P_s^{COP}(q)=(q_x,q_z)^T+l_f(-\sin(\phi),\cos(\phi))^T=S(\phi+\Theta_a)P_s,$$

where S is the standard rotation matrix parameterized by angle $\varphi+\Theta_a$:

$$S(\varphi+\Theta_a)=[\cos(\varphi+\Theta_a),-\sin(\varphi+\Theta_a)\sin(\varphi+\Theta_a),\cos(\varphi+\Theta_a)].$$

In 509, microcontroller 100 then calculates the distance relationship $h_s(q)$, which represents effective shape error eA, as follows:

$$h_s(q):=R_s-\text{norm}(P_s^{COP}(q)).$$

In other words, $h_s(q)$ (also known herein as eA) is an output of the control system corresponding to tracking error, specifically the Euclidean distance from the desired AF effective shape.

In 509a, microcontroller 100 calculates the KAF effective center of rotation in the COP-based reference frame by the function:

$$P_t^{COP}(q)=(q_x,q_z)^T=l_f(-\sin(\phi),\cos(\phi))^T+S(\rho)P_t,$$

where rotation matrix S is parameterized by angle $$\rho = \phi + \arctan\left(\frac{l_s\sin(\theta_a) + l_t\sin(\theta_a + \theta_k)}{l_s\cos(\theta_a) + l_t\cos(\theta_a + \theta_k)}\right).$$

In 509b, microcontroller 100 calculates the distance relationship $h_t(q)$, which represents effective shape error eK, as follows:

$$h_t(q):=R_t-\text{norm}(P_t^{COP}(q)).$$

The $z_s$ component of $P_s$ is given by $Z_s=\sqrt{R_s^2-X_s^3}-l_f$ (i.e., a function of previously recorded values), and the $z_t$ component of $P_t$ is similarly given by $Z_t\sqrt{R_t^2-X_t^2}-l_f$. An expanded equation for calculating $h_s(q)$ is provided in the Equations Appendix.

Still referring to FIG. 5, in 510a, the joint-level loop 120 attempts to bring error eA to zero by causing motor 50a to apply an appropriate torque at the ankle joint 21. In 510b, the joint-level loop 120 attempts to bring error eK to zero by causing motor 50b to apply an appropriate torque at the knee joint 31. The steps the microcontroller 100 takes to determine the appropriate torques are discussed in further detail below.

Both the AF and KAF constraints depend on the COP, which moves monotonically from heel to toe during steady walking. Because joint level loop 120 virtually enforces both constraints, and as both constraints depend on COP as a phase variable, the torques that microcontroller 100 causes motors 50 to produce result in coordinating knee and ankle movement of prosthetic 10. Microcontroller 100 virtually enforces the AF and KAF constraints on prosthetic 10 by producing control torques that drive the errors eA and eK to zero. It should be apparent to one of ordinary skill in the art that eA could be calculated prior to, concurrently with, or after eK.

Determining Torque Controls

In one embodiment, joint torques outputted by motors 50 are determined by a proportional-derivative (PD) controller. In another embodiment, joint torques outputted by motors 50 are determined by a feedback linearization (FL) controller.

PD Controller.

FIG. 6a displays a flow chart indicating the steps that embodiments of the invention take to control torque using the PD controller. In 600, which represents an initialization step, a clinician uses a computer program or other user interface to transmit the patient's weight to microcontroller 100. Joint-level loop 120 assigns the default control gains as hs, ht in units of m, we chose the normalized PD gains $k_{pa}=k_{pk}=2$ N/kg, $k_{da}=k_{dk}=0.6$ sqrt(kpk), and $k_{dka}=-0.5k_{dk}$. The user interface allows the clinician to modify the values of $k_{pa}$ or $k_{pk}$, increasing or decreasing them to increase or decrease the stiffness of their respective joints. The user interface also allows the clinician to modify the values of $k_{da}$ or $k_{dk}$, increasing or decreasing them to increase or decrease their respective viscosity (i.e. the feeling of resistance to motion). The ankle and knee gains can be adjusted separately as desired.

In 601, joint-level loop 120 calculates eA and/or eK. In 602, joint-level loop 120 calculates the time-derivatives of eA and/or eK. In one embodiment, joint-level loop 120 calculates the time-derivatives using sensor measurements reflecting joint angles and velocities from encoders 40 and COP calculated from load cell system, according to the $\dot{h}_s$ and $\dot{h}_t$ equations in the Equation Appendix, which correspond to the analytical time-derivative of the eA and eK equations. Alternately, joint-level loop 120 may compute the time-derivatives of eA and eK by numerical differentiation of a time-history of previously calculated eA and eK values.

In 602, joint-level loop 120 uses the control gains in 600 and the time-derivatives of eA and eK in 602 to compute the desired torques for the motors 50. The joint-level loop 120 calculates joint torques tA and tK from sensor measurements reflecting joint angles and velocities from encoders 40 and COP calculated from load cell system, according to the following proportional-derivative (PD) control law:

$$\tau_a=-k_{pa}h_s(q)-k_{da}\dot{h}_s(q,\dot{q})$$

$$\tau_k=-k_{pk}h_t(q)-k_{dk}\dot{h}_t(q,\dot{q})-k_{dka}\dot{h}_s(q,\dot{q})$$

where $\dot{h}_s$ and $\dot{h}_t$ are the time-derivatives of eA and eK and the gains $k_{pa}$, $k_{pk}$, $k_{da}$, $k_{dk}$, and $k_{dka}$ (held constant during the stance period) determine the desired corrective torques $\tau_a$ (also known herein as tA) and $\tau_k$ (also known herein as tK) at the ankle and knee, respectively. Note that the knee torque includes an ankle damping term to facilitate knee flexion as the ankle rapidly plantarflexes during late stance.

Microcontroller 100 sends tA and tK to motor-level loop 110, which as described above causes motors 50 to produce torques that move the ankle and knee joints.

The PD control law depends on the COP through calculations of eA and eK. As the COP moves monotonically from heel to toe, during steady walking, the COP serves as the phase variable of this controller and therefore control behavior will change continuously with the gait cycle phase, allowing a single equation to control the entire stance period.

The PD controller may be preferable for less demanding tasks such as standing or walking, although it may be used for other tasks as well. An alternate torque controller, the feedback linearization controller, may be used instead, which uses an intrinsic model of the leg that consists of mass/inertia information for each segment of the leg and friction/viscosity of each joint. The alternate torque controller regulates effective shapes to zero tracking error and so may be used for more demanding tasks in some patients, such as running.

Feedback Linearization Controller.

In one embodiment, microcontroller 100 determines joint torques tA and tK using an interaction force vector F and an intrinsic model of the prosthetic leg.

In 701, microcontroller 100 measures interaction force F. In one embodiment, a 3-axis load cell 60 is coupled to the socket connecting limb 10 to the patient's residual limb. In another embodiment, force F is estimated from loads measured at the foot and torques of the ankle and knee joints according to rigid-body dynamics.

In 702, microcontroller 100 computes a constraint matrix A modeling foot motion. Microcontroller 100 first models the heel point x, y along an arc that has radius $R_f$ and intersects the COP by the equation $$a_1^{roll}(q) := (x - R_f \sin(\phi))^2 + (y + R_f \cos(\phi))^2 - R_f^2.$$

Microcontroller 100 then models the foot orientation $\varphi$ so the heel is perpendicular to the foot, where $a_2^{roll}(q) = 0$ for $$a_2^{roll}(q) := \phi - \gamma - 2\arcsin\left(\frac{\sqrt{x^2 + y^2}}{2R_f}\right)$$

on a ground slope of angle γ. The standard method in R. M. Murray, Z. Li, and S. Sastry, A Mathematical Introduction to Robotic Manipulation. Boca Raton: CRC Press, 1994 ("Sastry"), incorporated by reference, is used to compute the constraint matrix $A = \nabla_q a$.

In 703, microcontroller 100 computes a Lagrange multiplier $\lambda = \hat{\lambda} + \tilde{\lambda}u + \bar{\lambda}F$ where (omitting matrix arguments)

$$\hat{\lambda} = W(\dot{A}\dot{q} - AM^{-1}(C\dot{q} + N)),$$

$$\tilde{\lambda} = WAM^{-1}B, \bar{\lambda} = WAM^{-1}J^T$$

for $W = (AM^{-1}A^T)^{-1}$. Here, M is the inertia/mass matrix, C is the matrix of Coriolis/centrifugal terms, N is the vector of gravitational forces, A is the constraint vector for the foot model, and λ is the Lagrange multiplier consisting of physical forces from the foot constraint. It is assumed these terms have been modeled using the standard methods in Sastry based on knowledge of the mass and inertia for each segment of the prosthetic leg. The matrix $B = (0_{2\times 3}, I_{2\times 2})^T$ for direct motor-to-joint actuation. An additional term can be added to these dynamics to model joint friction/viscosity.

In 704, microcontroller 100 computes the following vector fields:

$$f(z) = \begin{pmatrix} \dot{q} \\ -M(q)^{-1}(C(q,\dot{q})\dot{q} + N(q) + A^T(q)\lambda) \end{pmatrix},$$

$$g(z) = \begin{pmatrix} 0_{5\times 5} \\ M^{-1}(q)B \end{pmatrix}, j(z) = \begin{pmatrix} 0_{5\times 5} \\ M^{-1}(q)J^T(q) \end{pmatrix}.$$

In 705, microcontroller 100 computes the following Lie derivatives:

$$\widetilde{L_f^2 h} = (\nabla_q L_f h)\dot{q} - (\nabla_q L_f h)M^{-2}(C\dot{q} + N + A^T\hat{\lambda})$$

$$\widetilde{L_f^2 h} = -(\nabla_q L_f h)M^{-1}A^T\tilde{\lambda}, \overline{L_f^2 h} = -(\nabla_q L_f h)M^{-1}A^T\bar{\lambda}.$$

In 706, microcontroller 100 computes eA and eK and their time-derivatives as described in FIGS. 5 and 6*a*. eA and eK are assigned to a vector array y=[eA, eK]. In 707, microcontroller 100 computes an auxiliary input v:

$$v := -\begin{pmatrix} K_{ps} & 0 \\ 0 & K_{pt} \end{pmatrix}\xi - \begin{pmatrix} K_{ds} & 0 \\ 0 & K_{dt} \end{pmatrix}\dot{\xi},$$

with positive PD gains as defined by a clinician in 600 and where $\dot{\xi} = \dot{h}(z) = (\dot{h}_s(z), \dot{h}_t(z))^T$, $\xi := h(z) = (h_s(z), h_t(z))^T$, and z is the state vector (q, $\dot{q}$).

In 708, microcontroller 100 uses the Lie derivative terms to compute the desired joint torques tA and tK at the motors 50:

$$u_{st} = D^{-1}(-\widetilde{L_f^2 h} - (\overline{L_f^2 h} + L_j L_f h)F + v)$$

where the decoupling matrix $D = L_g L_f h + \widetilde{L_f^2 h}$. The advantage of this controller is that it renders linear the dynamics of errors eA and eK, by which the control torques tA and tK to motors 50 drive the errors to zero exponentially fast.

Enforcing the effective shape results in advantages when enforced on certain embodiments described herein. FIG. 8 displays graph of torque profiles produced by limb 10 when enforcing effective shapes AF and KAF and utilizing the PD controller. When in use, the ankle angle trajectory starts with a short period of controlled plantarflexion, as the foot progresses from heel-strike to foot-flat. Subsequently, as the leg 15 rotates over foot 70, ankle 20 begins to dorsiflex until a peak of about 12 degrees is reached at about 70% of stance. After this point, the movement reverses, and ankle 20 starts to actively plantarflex, as indicated by the torque profile in FIG. 8. The torque profile indicates that the additional torque from motors 50, caused by microcontroller 100's enforcement of the virtual constraints, provides a powered push-off at the end of stance, thus contributing actively to the energetics of walking.

FIG. 9 plots the knee joint flexion in limb 10 operating under AF and KAF virtual constraints. In early stance, the knee joint exhibits less flexion when compared to natural gait, due to the prosthetic wearer locking the knee while loading his/her body weight on the leg. Locking the knee is a common strategy for prosthesis users to ensure the knee does not buckle at this critical point in the gait. Late-stance knee flexion is close to natural and in synergy with ankle push-off, allowing the transfer of positive propulsive energy to the user. Enforcing the effective shape provides a natural period of power generation as the COP approaches the toe. A positive feedback loop arises when COP movement causes a plantarflexive ankle torque, which in turns causes the COP to move further forward. During early stance this positive loop is counteracted by a negative loop involving the moment arm from shear forces. This biomimetic behavior, resembling that of more complex muscle reflex models, can prevent compensatory work at the hip, allowing lower-limb amputees to expend levels of energy when walking comparable to a person with a sound limb. Data from the prosthesis displayed in FIGS. 8A, 8B, and 9 are compared to able bodied limb data from Winter.

FIGS. 14B and 14B display mechanical power plots for the ankle and knee, respectively, when in use and controlling torque using the PD controller. FIG. 14A shows that the control system described herein causes limb 10 to perform a substantial amount of positive mechanical work, thus contributing to the energetic of gait and significantly reducing the amount of effort a patient would otherwise expend to walk or perform another task. FIG. 14B shows that the additional power provided at the ankle does not come at the expense of power from the knee, which does more or less net zero work (the integral of power over time), as desired.

FIG. 15A displays a phase portrait (plotting angular positions vs. velocities) for the ankle joint, reflecting 20 gait cycles from a treadmill experiment. Stance period is shown as solid line and swing is shown as a dashed line. As indicated in FIG. 15A, ankle trajectories converge to a periodic orbit—known as a limit cycle—as the subject's gait approached steady state. This result indicates that a lower limb device utilizing the control strategies described herein is robust against external physical stimuli; a patient using the device enjoys a certain level of physical stability and the device returns to periodic orbit in the event of a push to the subject or other external, unanticipated force. Note that most of the variability occurs during the swing period, when the prosthesis employed a prior art sequential impedance controller and without the control strategies described herein. FIG. 15B displays a similar phase portrait for the knee joint, from the same treadmill experiment.

As described above, limb 10 employs a stance controller only during the stance period, as detected by the vertical force measured by the load cells. When the load drops below a threshold (e.g., 20% body weight), limb 10 enters the swing period. Because the foot of the limb does not press against the ground during the swing period, COP is not defined during that period. Nonetheless, in one embodiment of the invention, a prosthetic control system may nonetheless employ phase-based virtual constraints during the swing period, as described below.

In one embodiment, the COP of the limb 10 is measured from the contralateral leg 5, which is in stance. If contralateral leg 5 is also artificial, such as a prosthetic, then contralateral leg 5 may communicate COP measurements to limb 10 while limb 10 is in swing. If contralateral leg 5 is a sound limb, then force sensors may be coupled to the sole of the foot coupled to contralateral leg 5, which transmit COP measurements to limb 10. Such force sensors may be attached to a specialized shoe or other footwear. In each case, the limb 10, while in the swing period, could then control a phase-based virtual constraint that corresponds to swing motions.

In another embodiment, the swing limb 10 employs a phase variable, other than the COP, that is measurable from the limb during swing. For instance, the position of the thigh (which moves monotonically forward) could be measured from an inertial measurement unit at the socket of the prosthesis. A virtual constraint that defines joint motion as a function of this phase variable could then be used to control the swing period.

The transition to swing phase can be assisted by preventing the knee from producing extensor torques during the double-support period of gait, defined as the period when both legs are in contact with the ground. This can be achieved by saturating the knee torque above zero if extension corresponds to negative torque or below zero if extension corresponds to positive torque in the given control system. The double-support period can be detected by a decrease in the vertical load measured by the load cells in the prosthetic leg.

The control strategy described herein can regulate the effective shapes for different tasks including inclined walking and stair climbing. For this purpose the controller can employ the general model of effective shape, allowing non-constant curvature in the effective shapes defining eA and eK. Effective shape control could then be integrated with a neural interface (for instance, using electromyography from residual muscles) to allow the user to subconsciously adapt the effective shapes when anticipating a task change.

APPENDIX OF DETAILED EQUATIONS

It should be apparent to one of ordinary skill in the art that the q terms index values from configuration vector array are defined herein as follows: $q=(qx, qz, \varphi, \Theta_a, \Theta_k)^T$. All x terms index values from the state vector array $x=(q,\dot{q})$. The following variables represent the following values: lt (thigh length); ls (shank length); la (heel-to-ankle length); Rt and Rs (KAF and AF effective radius); Xt (KAF center of rotation); Xs (AF center of rotation).

$$h_s = Rs\text{-}sqrt((Xs.*\cos(q(3)+q(4))+(-1).*la.*\sin(q(3))+$$
$$(-1).*\ldots Ys.*\sin(q(3)+q(4))+q(1)).\wedge 2+$$
$$(la.*\cos(q(3))+Ys.*\cos(q(3)+q(4)\ldots)+$$
$$Xs.*\sin(q(3)+q(4))+q(2)).\wedge 2));$$

$$h_t = Rt\text{-}sqrt((Xt.*\cos(\text{atan}((ls.*\cos(q(4))+lt.*\cos(q(4)+q(\ldots 5))).\wedge$$
$$(-1).*(ls.*\sin(q(4))+lt.*\sin(q(4)+q(5))))+$$
$$q(3))+(-1).*\ldots la.*\sin(q(3))+(-1).*Yt.*$$
$$\sin(\text{atan}((ls.*\cos(q(4))+lt.*\cos(\ldots q(4)+q(5))).\wedge$$
$$(-1).*(ls.*\sin(q(4))+lt.*\sin(q(4)+q(5))))+$$
$$q(3))\ldots +q(1)).\wedge 2+(la.*\cos(q(3))+Yt.*$$
$$\cos(\text{atan}((ls.*\cos(q(4))+lt.*\ldots\cos(q(4)+q(5))).\wedge(-1).*$$
$$(ls.*\sin(q(4))+lt.*\sin(q(4)+q(5))))+\ldots q(3))+$$
$$Xt.*\sin(\text{atan}((ls.*\cos(q(4))+lt.*\cos(q(4)+q(5))).\wedge$$
$$(\ldots -1).*(ls.*\sin(q(4))+$$
$$lt.*\sin(q(4)+q(5))))+q(3))+q(2)).\wedge 2));$$

$$h_s = -(1/2).*((Xs.*\cos(x(3)+x(4))+(-1).*la.*\sin(x(3))+$$
$$(-1).*\ldots Ys.*\sin(x(3)+x(4))+x(1)).\wedge 2+$$
$$(la.*\cos(x(3))+Ys.*\cos(x(3)+x(4)\ldots)+$$
$$Xs.*\sin(x(3)+x(4))+x(2)).\wedge 2).\wedge(-1/2).\wedge(-1/2).*$$
$$\ldots (2.*(Xs.*\cos(x(3)+x(4))+(-1).*la.*\sin(x(3))+$$
$$(-1).*Ys.*\sin(x(\ldots 3)+x(4))+x(1)).*$$
$$(x(6)+(-1).*la.*\cos(x(3)).*x(8)+$$
$$(-1).*Ys.*\ldots \cos(x(3)+x(4)).*(x(8)+x(9))+$$
$$(-1).*Xs.*\sin(x(3)+x(4)).*(x(\ldots 8)+x(9)))+$$
$$2.*(la.*\cos(x(3))+Ys.*\cos(x(3)+x(4))+$$
$$Xs.*\sin(x(\ldots 3)+x(4))+x(2)).*$$
$$(x(7)+(-1).*la.*\sin(x(3)).*x(8)+$$
$$Xs.*\cos(x(\ldots 3)+x(4)).*(x(8)+x(9))+$$
$$(-1).*Ys.*\sin(x(3)+x(4)).*(x(8)+x(\ldots 9))));$$

-continued $$h_{th} = -(1/2).*((Xt.*\cos(\text{atan}((ls.*\cos(x(4))+lt.*\cos(x(4)+x(\ldots 5)))).^{\wedge}$$
$$(-1).*(ls.*\sin(x(4))+lt.*\sin(x(4)+x(5)))) +$$
$$x(3))+(-1).*\ldots la.*\sin(x(3))+(-1).*Yt.*$$
$$\sin(\text{atan}((ls.*\cos(x(4))+lt.*\cos(\ldots x(4)+x(5)))).^{\wedge}(-1).*$$
$$(ls.*\sin(x(4))+lt.*\sin(x(4)+x(5))))+x(3))$$
$$\ldots +x(1)).^{\wedge}2+(la.*\cos(x(3))+Yt.*$$
$$\cos(\text{atan}((ls.*\cos(x(4))+lt.*\ldots \cos(x(4)+x(5)))).^{\wedge}(-1).*$$
$$(ls.*\sin(x(4))+lt.*\sin(x(4)+x(5))))+\ldots x(3)) +$$
$$Xt.*\sin(\text{atan}((1s.*\cos(x(4))+lt.*\cos(x(4)+x(5)))).^{\wedge}$$
$$(\ldots -1).*$$
$$(ls.*\sin(x(4))+lt.*\sin(x(4)+x(5)))) +$$
$$x(3))+x(2)).^{\wedge}2).^{\wedge}(-1/2).*\ldots$$
$$(2.*(Xt.*\cos(\text{atan}((ls.*\cos(x(4))+lt.*\cos(x(4))+lt.*$$
$$\cos(x(4)+x(5)))).^{\wedge}(-1).*$$
$$(\ldots ls.*\sin(x(4))+lt.*\sin(x(4)+x(5))))+x(3)) +$$
$$(-1).*la.*\sin(x(3))\ldots+(-1).*Yt.*$$
$$\sin(\text{atan}((ls.*\cos(x(4))+lt.*\cos(x(4)+x(5)))).^{\wedge}(-1)$$
$$\ldots .*(ls.*\sin(x(4))+lt.*\sin(x(4)+x(5)))) +$$
$$x(3))+x(1)).*$$
$$(x(6)+(\ldots -1).*la.*\cos(x(3)).*x(8)+(-1).*Yt.*$$
$$\cos(\text{atan}((ls.*\cos(x(4))+\ldots lt.*\cos(x(4)+x(5)))).^{\wedge}$$
$$(-1).*(ls.*\sin(x(4)) +$$
$$lt.*\sin(x(4)+x(5))\ldots ))+x(3)).*$$
$$(ls.^{\wedge}2+lt.^{\wedge}2+2.*ls.*lt.*\cos(x(5))).^{\wedge}(-1).*$$
$$((ls.^{\wedge}2+\ldots lt.^{\wedge}2+2.*ls.*lt.*\cos(x(5))).*x(8) +$$
$$(ls.^{\wedge}2+lt.^{\wedge}2+2.*ls.*lt.*\ldots \cos(x(5))).*x(9) +$$
$$lt.*(lt+ls.*\cos(x(5))).*x(10))+(-1).*Xt.*$$
$$(\ldots ls.^{\wedge}2+lt.^{\wedge}2+2.*ls.*lt.*\cos(x(5))).^{\wedge}(-1).*$$
$$\sin(\text{atan}((ls.*\cos(\ldots x(4))+lt.*\cos(x(4)+x(5)))).^{\wedge}$$
$$(-1).*\sin(x(4))+lt.*$$
$$\sin(x(4)\ldots +x(5))))+x(3)).*$$
$$((ls.^{\wedge}2+lt.^{\wedge}2+2.*ls.*lt.*\cos(x(5))).*x(8) +$$
$$(\ldots ls.^{\wedge}2+lt.^{\wedge}2+2.*ls.*lt.*\cos(x(5))).*x(9) +$$
$$lt.*(lt+ls.*\cos(x(\ldots 5))).*x(10))) +$$
$$2.*(la.*\cos(x(3))+Yt.*\cos(\text{atan}((ls.*\cos(x(4)) +$$
$$\ldots lt.*\cos(x(4)+x(5)))).^{\wedge}(-1).*$$
$$(ls.*\sin(x(4))+lt.*\sin(x(4)+x(5))\ldots ))+x(3)) +$$
$$Xt.*\sin(\text{atan}((ls.*\cos(x(4))+lt.*\cos(x(4)+x(5)))).^{\wedge}$$
$$(\ldots -1).*(ls.*\sin(x(4))+lt.*$$
$$\sin(x(4)+x(5))))+x(3))+x(2)).*$$
$$(x(7)\ldots +(-1).*la.*\sin(x(3)).*x(8)+Xt.*$$
$$\cos(\text{atan}((ls.*\cos(x(4))+lt.*\ldots \cos(x(4)+x(5)))).^{\wedge}(-1).*$$
$$(ls.*\sin(x(4))+lt.*\sin(x(4)+x(5))))+\ldots x(3)).*$$
$$(ls.^{\wedge}2+lt.^{\wedge}2+2.*ls.*lt*\cos(x(5))).^{\wedge}(-1).*$$
$$((ls.^{\wedge}2+\ldots lt.^{\wedge}2+2.*ls.*lt.*\cos(x(5))).*x(8) +$$
$$(ls.^{\wedge}2+lt.^{\wedge}2+2.*ls.*lt.*\ldots \cos(x(5))).*x(9) +$$
$$lt.*(lt+ls.*\cos(x(5))).*x(10))+(-1).*Yt.*$$
$$(\ldots ls.^{\wedge}2+lt.^{\wedge}2+2.*ls.*lt.*\cos(x(5))).^{\wedge}(-1).*$$
$$\sin(\text{atan}((ls.*\cos(\ldots x(4))+lt.*\cos(x(4)+x(5)))).^{\wedge}(-1).*$$
$$(ls.*\sin(x(4))+lt.*\sin(x(4)\ldots +x(5))))+x(3)).*$$
$$((ls.^{\wedge}2+lt.^{\wedge}2+2.*ls.*lt.*\cos(x(5))).*x(8) +$$
$$(\ldots ls.^{\wedge}2+lt.^{\wedge}2+2.*ls.*lt.*\cos(x(5))).*x(9) +$$
$$lt.*(lr+ls.*\cos(x(\ldots 5))).*x(10))));$$

What is claimed is:

1. A method for controlling a lower limb device, the method comprising:
receiving load information from at least one load sensor in operative communication with a microcontroller, wherein the load information reflects a load placed on the lower limb device by a user of the lower limb device;
determining a center of pressure of the lower limb device based on at least a portion of the load information;
determining an effective shape associated with the lower limb device; and
adjusting, by the microcontroller, at least one joint element associated with at least one joint of the lower limb device to move the center of pressure in order to match a position of the lower limb device to the effective shape of the user of the lower limb device.

2. The method of claim 1, wherein the method is used to control the lower limb device in its stance phase.

3. The method of claim 1, wherein the method is used to control the lower limb device in its swing phase.

4. The method of claim 1, wherein the at least one joint adjusted comprises a knee joint and an ankle joint.

5. The method of claim 1, wherein the at least one joint is adjusted by applying a torque to the at least one joint.

6. The method of claim 1, wherein the position of the lower limb device is matched to the effective shape by minimizing an effective shape error.

7. The method of claim 6, wherein the least one joint element is adjusted by applying a torque setting determined by a proportional-derivative controller.

8. The method of claim 6, wherein the at least one joint element is adjusted by applying a torque in an amount that is determined by a feedback-linearization controller.

9. The method of claim 1, wherein the moving of the center of pressure in order to match the position of the lower limb device to the effective shape comprises maintaining a fixed distance between the center of pressure and a pre-determined point in a shank-based reference frame during stance phase of the lower limb device.

10. The method of claim 9, wherein the fixed distance between the center of pressure and the pre-determined point is proportional to a height of the user.

11. The method of claim 9, wherein the fixed distance between the center of pressure and the pre-determined point is equal to a product of 0.158 and a height of the user in meters.

12. The method of claim 1, wherein the moving of the center of pressure in order to match the position of the lower limb device to the effective shape comprises maintaining a pre-defined distance between the center of pressure and a pre-determined point in a shank-based reference frame during stance phase of the lower limb device.

13. The method of claim 12, wherein the pre-defined distance between the center of pressure and the pre-determined point is defined as a function of the center of pressure.

14. The method of claim 1, wherein the moving of the center of pressure in order to match the position of the lower limb device to the effective shape comprises maintaining a fixed distance between the center of pressure and a pre-determined point in a thigh-based reference frame during stance phase of the lower limb device.

15. The method of claim 14, wherein the fixed distance between the center of pressure and the pre-determined point is proportional to a height of the user.

16. The method of claim 15, wherein the fixed distance between the center of pressure and the pre-determined point is equal to a product of 0.158 and a height of the user in meters.

17. The method of claim 1, further comprising maintaining a pre-defined distance between the center of pressure and a pre-determined point in a thigh-based reference frame during a stance phase of the lower limb device.

18. The method of claim 17, wherein the pre-defined distance between the center of pressure and the pre-determined point is defined as a function of the center of pressure.

19. The method of claim 1, wherein the effective shape includes an ankle-foot effective shape.

20. The method of claim 1, wherein the effective shape includes a knee-ankle-foot effective shape.

21. The method of claim 1, further comprising:
wherein the effective shape defines a trajectory associated with the center of pressure mapped into a reference frame associated with the lower limb device,
wherein the center of pressure defines a phase variable associated with the microcontroller such that changes to the center of pressure define corresponding changes to the at least one joint element, and
wherein, as part of a joint level loop, the microcontroller processes and instructs a motor to apply the changes to the at least one joint element to virtually enforce the effective shape and minimize effective shape errors resulting in coordinating ankle and knee movements of the lower limb device.

22. A lower limb device, comprising: a load sensor, a joint element, a motor, and a microcontroller programmed with instructions for:
receiving load information from at least one load sensor in operative communication with a microcontroller, wherein the load information reflects a load placed on the lower limb device;
determining a center of pressure of the lower limb device based on at least a portion of the load information;
determining an effective shape; and
adjusting at least one joint element associated with at least one joint of the lower limb device to move the center of pressure in order to match a position of the lower limb device to the effective shape of the lower limb device
wherein the microcontroller instructs the motor to apply the at least one joint element of the lower limb device as adjusted.

23. The lower limb device of claim 22, wherein the at least one joint element includes a torque.

24. The lower limb device of claim 23, wherein the at least one joint includes a powered ankle joint or a powered knee joint.

* * * * *